(12) United States Patent
Sim

(10) Patent No.: US 11,576,943 B2
(45) Date of Patent: Feb. 14, 2023

(54) FUNCTIONAL FOOD COMPOSITION HAVING CRANIAL NERVE PROTECTION EFFECT AND BLOOD FLOW IMPROVEMENT EFFECT

(71) Applicant: chzin Co., Ltd., Wonju-si (KR)

(72) Inventor: Mansub Sim, Seoul (KR)

(73) Assignee: chzin Co., Ltd., Wonju-si (KR)

( * ) Notice: Subject to any disclaimer, the term of this patent is extended or adjusted under 35 U.S.C. 154(b) by 0 days.

(21) Appl. No.: 17/327,574

(22) Filed: May 21, 2021

(65) Prior Publication Data

US 2022/0088108 A1    Mar. 24, 2022

(30) Foreign Application Priority Data

Sep. 18, 2020   (KR) .................. 10-2020-0120420

(51) Int. Cl.

| | | |
|---|---|---|
| A61K 36/75 | (2006.01) | |
| A61K 36/232 | (2006.01) | |
| A61K 36/40 | (2006.01) | |
| A61K 36/64 | (2006.01) | |
| A61K 36/31 | (2006.01) | |
| A61K 36/734 | (2006.01) | |
| A61K 45/06 | (2006.01) | |
| A61K 36/83 | (2006.01) | |
| A61K 36/65 | (2006.01) | |
| A61K 35/36 | (2015.01) | |
| A61K 9/00 | (2006.01) | |
| A61K 47/26 | (2006.01) | |
| A61P 7/00 | (2006.01) | |
| A61K 36/48 | (2006.01) | |

(52) U.S. Cl.
CPC ............ *A61K 36/75* (2013.01); *A61K 9/0095* (2013.01); *A61K 35/36* (2013.01); *A61K 36/232* (2013.01); *A61K 36/31* (2013.01); *A61K 36/40* (2013.01); *A61K 36/48* (2013.01); *A61K 36/64* (2013.01); *A61K 36/65* (2013.01); *A61K 36/734* (2013.01); *A61K 36/83* (2013.01); *A61K 45/06* (2013.01); *A61K 47/26* (2013.01); *A61P 7/00* (2018.01)

(58) Field of Classification Search
None
See application file for complete search history.

(56) References Cited

FOREIGN PATENT DOCUMENTS

| KR | 10-2002-0012435 A | 2/2002 |
|---|---|---|
| KR | 10-2005-0101818 A | 10/2005 |
| KR | 101227063 B1 | 1/2013 |
| KR | 10-1645855 B1 | 8/2016 |

OTHER PUBLICATIONS

KR101227063B1 (English translation retrieved from Google Patents) (Year: 2012).*

* cited by examiner

*Primary Examiner* — Michael Barker
(74) *Attorney, Agent, or Firm* — Heedong Chae; Lucem, PC

(57) ABSTRACT

One aspect of the present disclosure relates to a functional food composition having a cranial nerve protective effect and a blood flow improvement effect and including antler, an *Angelica gigas* root, a *Cornus officinalis* fruit, a *Rehmannia glutinosa* root, *Lepidium meyenii* root powder, a hawthorn fruit, an *Astragalus membranaceus* root, a cod seed, aloeo wood, a *Paeonia lactiflora* root, a *Cnidium officinale* root stem and a *Citrus reticulata* shell.

2 Claims, 1 Drawing Sheet

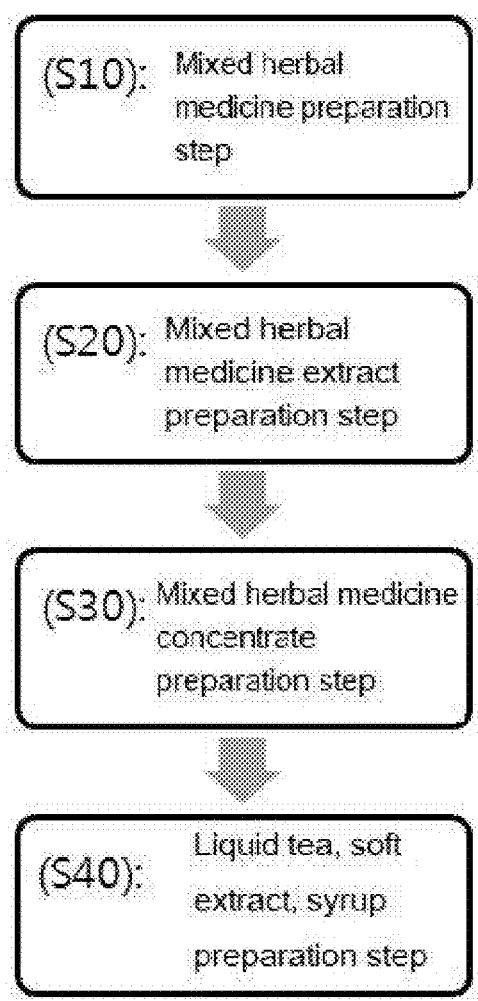

FUNCTIONAL FOOD COMPOSITION HAVING CRANIAL NERVE PROTECTION EFFECT AND BLOOD FLOW IMPROVEMENT EFFECT

CROSS-REFERENCE TO RELATED APPLICATIONS

This application claims the priority of Korean Patent Application No. 10-2020-0120420 filed on Sep. 18, 2020, in the Korean Intellectual Property Office, the disclosure of which is incorporated herein by reference.

BACKGROUND

1. Field

One aspect of the present disclosure relates to a food composition, and more specifically, to a functional food composition having a cranial nerve protective effect and a blood flow improvement effect and including antler, an *Angelica gigas* root, a *Cornus officinalis* fruit, a *Rehmannia glutinosa* root, *Lepidium meyenii* root powder, a hawthorn fruit, an *Astragalus membranaceus* root, a cod seed, aloeo wood, a *Paeonia lactiflora* root, a *Cnidium officinale* root stem and a *Citrus reticulata* shell.

2. Description of Related Art

The circulation of blood refers to the process of circulating the blood along blood vessels of a human body around the heart to supply oxygen to each tissue of the human body, release carbon dioxide, supply nutrients, release metabolites, carry hormones from endocrine glands to control functions of specific organs, and perform functions such as pathogen control, body temperature control, osmotic pressure control, and moisture control. Blood vessels consist of arteries, capillaries, and veins. The artery includes an outer membrane consisting of an outer elastic sheath and a connective tissue, a medial membrane mainly consisting of smooth muscles containing a number of elastic fibers therein, and an inner membrane in the form of a stiffness plate consisting of innermost endothelial cells, the connective tissue surrounding the innermost endothelial cells and elastic fibers. The capillary is formed through the connection of arterioles and prescribed veins, in which the capillary is thinly branched in a net shape, and is formed of a thin tube with a diameter of 0.008 to 0.02 mm that allows red blood cells to pass therethrough in one or two rows. The capillary is not visible to the naked eye, oxygen and nutrients in the blood are sent into the tissues through the capillary, and $CO_2$ or waste products made from the tissues enter the blood vessels. Because the outer membrane of the vein is relatively thick and the inner membrane and the middle membrane are thin with no pressure and weaker blood flow than other blood vessels, there is a risk of reflux from the vein located below the heart, so a valve for preventing reflux is attached.

The blood circulation disorder means that the blood vessels extending through the human body lose elasticity and cholesterol is deposited on the inner wall, which narrows the lumen of blood vessels, making blood circulation difficult. The blood circulation disorder causes cold constitution and numbness in hands and feet, stiffness in back neck, stiff shoulders, memory loss, lethargy, weakened concentration, dizziness and chronic fatigue, making it difficult to have a normal life.

In order to solve the above problems, Korean Patent Registration Publication No. 10-1227063 discloses a food composition for improving blood circulation and a method for preparing the same, in which flaxseed, buckwheat, wormwood, *Ginkgo biloba*, pine needles, *Cassia* seed, licorice, mint, malt, rice, adlay, and *Camellia* are mixed with each other at an amount of 1 part by weight, brown sugar and alcohol are added thereto, and natural fermentation is performed to prepare the food composition.

However, the conventional food composition for improving blood circulation has a weak effect for protecting cranial nerves and improving blood circulation, and thus there is a need for research on a novel composition having an effect of protecting cranial nerves and improving blood circulation.

RELATED ART DOCUMENT

Patent Document (Patent Document 0001) Korean Patent Registration Publication No. 10-1227063 (issued on Jan. 29, 2013), "Food composition for improving blood circulation and preparation method thereof"

SUMMARY

In order to solve the above problems, an object of one aspect of the present disclosure is to provide a functional food composition having a cranial nerve protective effect and a blood flow improvement effect and including antler, an *Angelica gigas* root, a *Cornus officinalis* fruit, a *Rehmannia glutinosa* root, *Lepidium meyenii* root powder, a hawthorn fruit, an *Astragalus membranaceus* root, a cod seed, aloeo wood, a *Paeonia lactiflora* root, a *Cnidium officinale* root stem and a *Citrus reticulata* shell.

In order to achieve the above object, one aspect of the present disclosure provides a method of preparing a functional food composition having a cranial nerve protective effect and a blood flow improvement effect, the method including: a mixed herbal medicine preparation step (S10) of preparing a mixed herbal medicine by mixing antler, an *Angelica gigas* root, a *Cornus officinalis* fruit, a *Rehmannia glutinosa* root, *Lepidium meyenii* root powder, a hawthorn fruit, an *Astragalus membranaceus* root, a cod seed, aloeo wood, a *Paeonia lactiflora* root, a *Cnidium officinale* root stem and a *Citrus reticulata* shell; a mixed herbal medicine extract preparation step (S20) of preparing a mixed herbal medicine extract by extracting the mixed herbal medicine of step (S10) in a vacuum state; a mixed herbal medicine concentrate preparation step (S30) of preparing a mixed herbal medicine concentrate by concentrating the mixed herbal medicine extract of step (S20); and a liquid tea, soft extract, and syrup preparation step (S40) of preparing liquid tea, soft extract, and syrup preparing by mixing the mixed herbal medicine concentrate of step (S30) with oligosaccharides and DL-menthol.

In mixed herbal medicine preparation step (S10), the mixed herbal medicine may include 1 to 5% by weight of the antler, 1 to 5% by weight of the *Angelica gigas* root, 1 to 5% by weight of the *Cornus officinalis* fruit, 3 to 7% by weight of the *Rehmannia glutinosa* root, 3 to 7% by weight of the *Lepidium meyenii* root powder, 3 to 7% by weight of the hawthorn fruit, 1 to 5% by weight of the *Astragalus membranaceus* root, 0.1 to 2% by weight of the cod seed, 0.1 to 2% by weight of the aloeo wood, 1 to 5% by weight of the Paeonia lactiflora root, 1 to 2% by weight of the Cnidium officinale root stem and 1 to 5% by weight of the Citrus reticulata shell.

In mixed herbal medicine extract preparation step (S20), the mixed herbal medicine may be extracted in a vacuum state by adding an extraction solvent of at least one of water, alcohol having 1 to 4 carbon atoms, methanol, ethanol, butanol or propanol.

In liquid tea, soft extract, and syrup preparation step (S40), the oligosaccharide may be isomalto oligosaccharide.

In addition, one aspect of the present disclosure provides a functional food composition having a cranial nerve protective effect and a blood flow improvement effect prepared through the above preparation method.

The functional food composition having a cranial nerve protective effect and a blood flow improvement effect according to one aspect of the present disclosure includes antler, an *Angelica gigas* root, a *Cornus officinalis* fruit, a *Rehmannia glutinosa* root, *Lepidium meyenii* root powder, a hawthorn fruit, an *Astragalus membranaceus* root, a cod seed, aloeo wood, a *Paeonia lactiflora* root, a *Cnidium officinale* root stem and a *Citrus reticulata* shell, so that the cranial nerve protective effect and a blood flow improvement effect can be enhanced.

BRIEF DESCRIPTION OF THE DRAWINGS

FIG. 1 is a flowchart showing a preparing process of a functional food composition having a cranial nerve protective effect and a blood flow improvement effect according to one aspect of the present disclosure.

DETAILED DESCRIPTION OF THE EMBODIMENTS

The following detailed description of one aspect of the present disclosure is an embodiment which can be implemented by the present disclosure and will be described as an example of a corresponding embodiment with reference to the accompanying drawings. The embodiments will be described in detail to enable those skilled in the art to carry out the present disclosure. It is apparent to be understood that the various embodiments of the present disclosure may be different from each other but do not need to be mutually exclusive. For example, the particular shape, structure, and feature described herein may be embodied in other embodiments without departing from the idea and scope of the present disclosure in connection with the embodiment. In addition, it shall be understood that the location or arrangement of an individual element within each disclosed embodiment may be modified without departing from the idea and scope of the present disclosure. Accordingly, the following detailed description does not disclose a limited meaning, and the scope of the disclosure is limited only by the appended claims, along with the full scope of equivalents to which the claims are entitled, if properly explained. Similar reference numerals in the drawings refer to the same or similar function throughout several aspects.

General term which is widely used recently has been selected in the present disclosure in consideration of the function according to the present disclosure as possible, however, the term may vary depending on the intention of those skilled in the art, judicial cases, the advent of new technology, or the like. In addition, in certain cases, the term may be arbitrarily selected by the applicant, and in this case, the meaning thereof will be described in detail in the relevant description of the disclosure. Therefore, the term used in the present disclosure needs to be defined based on the meaning of the term and contents throughout the present disclosure, not simply on the name of the term.

When one part "includes" one element in the present disclosure, unless particularly stated otherwise, the above expression does not exclude other elements, but may further include the other elements.

As shown in FIG. 1, a method of preparing a functional food composition having a cranial nerve protective effect and a blood flow improvement effect according to one aspect of the present disclosure includes a mixed herbal medicine preparation step (S10) of preparing a mixed herbal medicine by mixing antler, an *Angelica gigas* root, a *Cornus officinalis* fruit, a *Rehmannia glutinosa* root, *Lepidium meyenii* root powder, a hawthorn fruit, an *Astragalus membranaceus* root, a cod seed, aloeo wood, a *Paeonia lactiflora* root, a *Cnidium officinale* root stem and a *Citrus reticulata* shell; a mixed herbal medicine extract preparation step (S20) of preparing a mixed herbal medicine extract by extracting the mixed herbal medicine of step (S10) in a vacuum state; a mixed herbal medicine concentrate preparation step (S30) of preparing a mixed herbal medicine concentrate by concentrating the mixed herbal medicine extract of step (S20); and a liquid tea, soft extract, and syrup preparation step (S40) of preparing liquid tea, soft extract, and syrup preparing by mixing the mixed herbal medicine concentrate of step (S30) with oligosaccharides and DL-menthol.

In mixed herbal medicine preparation step (S10), the mixed herbal medicine may include antler, an *Angelica gigas* root, a *Cornus officinalis* fruit, a *Rehmannia glutinosa* root, *Lepidium meyenii* root powder, a hawthorn fruit, an *Astragalus membranaceus* root, a cod seed, aloeo wood, a *Paeonia lactiflora* root, a *Cnidium officinale* root stem and a *Citrus reticulata* shell.

Antler refers to a horn of a deer dried in the shade. The antler is used as an energetic medicine. The deer's antlers naturally fall in late spring, and new antlers grow in their place. The horns that have started to grow are called antlers. It is covered with soft and fine hairs, is warm, contains a lot of blood vessels, and is rich in calcium. In the field of oriental medicines, it is used as a valuable medicine. In autumn, calcium inside the antler is keratinized hardly, and these keratinized horns are less effective than antlers and are called hard antlers.

The *Angelica gigas* root refers to a root of *Angelica gigas*. The *Angelica gigas* is a biennial or triennial herb that grows in a relatively humid land. The fat root of the *Angelica gigas* contains milk-color juice and has a strong scent. The stem of the *Angelica gigas* is thick and straight, and grows to a height of about 2 m and has some branches. Large leaves of the *Angelica gigas* are located while being offset at each node and are divided into three branches once or twice. The divided leaf fragments of the *Angelica gigas* are split into 3 to 5 branches again with a medium depth. Sharp serrations are formed on the edge of the leaf. The bottom of the leaf stem of the *Angelica gigas* is spread widely to completely enclose the stem. Small flowers hanging to ends of the stems and branches of the *Angelica gigas* grow together to form an umbrella shape. A purple flower of the *Angelica gigas* has 5 petals, and the diameter is about 3 mm.

The *Cornus officinalis* fruit refers to a fruit of *Cornus officinalis*. The *Cornus officinalis* fruit is an oval-shaped drupe, which is initially green and ripens red in August to October. The seeds have a long oval shape with ridges. It is astringent and has a strong sour taste with a slight sweetness. It is harvested around the 23$^{rd}$ of October, in which the fleshes and seeds are separated such that the fleshes can be used as an ingredient for alcoholic beverages, teas, and herbal medicines. The flesh contains glycosides such as cornin, moroniside, loganin, tannin and saponin, and organic acids such as wine, apple and tartaric acids, as well as vitamin A and a large amount of sugar. The seed contains palmitic acid, oleic acid and linoleic acid. Among the ingredients, cornin is known to have the excitatory action of the parasympathetic nerve.

The *Rehmannia glutinosa* root refers to a root of the *Rehmannia glutinosa* ((GAERTNER) LIBOSCHITZ). The *Rehmannia glutinosa* is a perennial herbaceous plant belonging to Scrophulariaceae, and it is a Chinese plant with short hairs distributed over the whole area, in which the root is thick and extend laterally, and is used as medicinal materials in the field of oriental medicines. It is called crude *Rehmannia glutinosa* when it is used as it is, dry *Rehmannia glutinosa* when it is dried for use, and steam *Rehmannia glutinosa* when it is steamed with alcohol. Rhizome grows in clusters and has a long oval shape with an obtuse top and an acute bottom where a dull serration is formed at the edge thereof. Flowers bloom in June and July, and hangs at the end of the stalk in the form of raceme (the shape of a flower that has a spigot on a long flower stalk and blooms alternately). The root is used as a medicinal material in the field of oriental medicines, and it is called crude *Rehmannia glutinosa* when it is used as it is, dry *Rehmannia glutinosa* when it is dried for use, and steam *Rehmannia glutinosa* when it is steamed with alcohol. The medicinal ingredients contain catalpol and mannite, and include mannitol, stachyose, and glucose in the water-soluble part.

The *Lepidium meyenii* root powder refers to root powder of *Lepidium meyenii*. The *Lepidium meyenii* is a biennial plant belonging to Chinese cabbage family and originating from the Peruvian Andes. It was first discovered in the highlands near Lake Funin. It is eaten or used as a medicinal plant. The *Lepidium meyeniiis* also known as maca-maca or maino in Spanish, and it is also called ayak chichira or ayak willku in Quechua. Among the *Lepidium micranthum* group, the *Lepidium meyeniiis* only one that has a fleshy hypocotyl and is combined with a straight root to form a body. The *Lepidium meyeniiroot* has various sizes and shapes, and the hypocotyl has gold, white, red, purple, blue, black, and green colors. Since the seed of the parent plant has a root having a color the same as the color the parent plant, each color has genetic characteristics. White roots are the most widely grown, and in Peru, the white roots are popular due to the size and sweetness thereof. There is a lot of iodine in the dark roots. The red root has the effect of reducing the size of the prostate gland as a result of testing in rats.

The hawthorn fruit refers to a fruit of hawthorn (Chinese hawthorn). The hawthorn is a deciduous broad-leaved small arboreous tree belonging to dicotyledonous Rosacles Rosaceae, and the fruits are used for edible and medicinal purposes. The name 'hawthorn' means "*Chaenomeles japonica* grown in the mountain", however, the hawthorn and the *Chaenomeles japonica* actually belong to completely different species. In addition, it is also called a haw tree, hawthorn, red confectionery, sanjohong, chilgwangi, and chilgubae tree. It is distributed in Korea, Japan, China, and Siberia. In Korea, it grows wild in the national mountainous areas and is popular as a tree for landscaping because of its beautiful flowers and fruits. The fruit has also been used for edible and medicinal purposes since ancient times. In the field of oriental medicines, the hawthorn fruit is also called '*Crataegus* fruit'. It is said to be effective for indigestion, enteritis, low back pain, hemorrhoids, and lower abdominal pain if it is cut in half to remove the seeds and dried in the sun. In addition, since it contains a large amount of vitamin C, it is effective in relieving fatigue, improving immunity, preventing colds, and beautifying the skin. It contains polyphenols to help with antioxidant activity and anti-aging.

The *Astragalus membranaceus* root refers to a root of *Astragalus membranaceus*. The *Astragalus membranaceus* is a plant belonging to the legume family and is one of the herbal medicines that are widely used in the field of oriental medicines. In addition, the history of use for medicinal purposes is very long, more than 2000 years, and it is a herbal plant registered in 「Shinnongbonchogyeong」, the first herbal book. The *Astragalus membranaceus* acts on the spleen meridian, the lung meridian, the triple energizer meridian, and the kidney meridian. It energizes, stops sweating, makes urine well out, removes pus, and makes new flesh grow. Tonic action, Immune function regulation action, heart action, diuretic action, blood pressure lowering action, and anti-inflammatory action were found in the experiment. It is used as a remedy for a feeble constitution, after illness, hyperhidrosis, cold sweat, weary, stomach weary, pulmonary abscess, diabetes, edema, carbuncle, skin disease, blood deficiency, and visceroptosis.

The cod seed refers to a dried seed of *Amomum xanthoides* wallor *A. villosum* Lour. The taste of the cod is hot and the nature is warm. It acts on the spleen meridian, the stomach meridian, the lung meridian, the colon meridian, the small intestine meridian, the kidney meridian and the bladder meridian. It promotes the circulation of energy, stops pain, strengthens and warms the stomach. It also aids in digestion and stabilizes the fetus. It is used as a remedy for pain in the solar plexus and abdomen caused by indigestion or dyspepsia, vomiting, diarrhea, dysentery, and fetal anxiety. Especially, it is widely used for poor appetite and poor digestion. It is prepared in the form of powder, pills, and soup and 2 to 6 g is taken per a day.

The aloe wood refers to a wood where resin of *Aquilaria agallocha* roxburgh (Thymeleaceae) is deposited. It is also called aquilariae lignum. The aloe is a part that forms a histologically hard mass on the heartwood of an aloe tree by depositing naturally secreted resin on the aloe tree. It is also called an agilawood. CP says "it is a wood containing resin of *Aquilaria sinensis* Gilg. It is collected at any time of the year, and the wood containing resin is taken, and the parts that do not contain resin are removed and then dried in the shade".

The *Paeonia lactiflora* root refers to a root of *Paeonia lactiflora*. The *Paeonia lactiflora* is a perennial plant belonging to paeoniaceae, *Paeonia* of dicotyledons and grows in the mountainous area. Several stems come out of one plant and stand upright about 60 cm high, and the leaves and stems have no hairs. There are several roots, but they are thin and both ends have a pointed cylinder shape with a thick thickness. The leaves are alternately grown, and the bottom one is a compound leaf with three small leaves coming out twice. Small leaves have a lanceolate shape or an oval shape, but sometimes the leaves are split into 2-3 pieces, and the veins and petioles are red. The leaf of the upper part is simple in shape, in which the leaf is a single leaf or three small leaves come out from the leaf. The leaf surface is glossy, the back side is light green, and the edges are flat.

The *Cnidium officinale* root stem refers to a root stem of *Cnidium officinale*. The *Cnidium officinale* is available from China and is cultivated as a medicinal plant. It has a height of 30 to 60 cm, is hollow, and branches are slightly split. The leaves are alternate and compound leaves with 3 pinnates in 2 times, and the forked pieces are egg-shaped lanceolate with rather deep serrations. Root leaves and lower leaves have long petioles, and the lower part becomes a sheath to wrap the stem. Flowers bloom in August to September, have a white color, and form a double-lobed inflorescence. There are 5 petals rolled inward, 5 stamens and 1 pistil. There are 5 to 6 involucrums and involucels arranged in a row. The fruit opens, but does not mature. Between nodes in the ground, it looks like a mass having a length of 5 to 10 cm and a diameter of 3 to 5 cm and has a strong scent. It is effective for sedation, pain, tonic, etc., so it is used to treat headache, anemia, and women's diseases. In September to November, the root is taken and the leaves and stems are removed. Then, after drying the root in the sun, 3 to 6 g of the root is decocted for edible purpose or it is prepared in the form of a pill or powder.

The *Citrus reticulata* shell refers to a shell of a fruit of *Citrus reticulata*. The *citrus reticulata* is an evergreen small arboreous tree belonging to rutaceae and citrus. The *citrus reticulata* has a low height, the development of the main stem (original stem) is difficult, the branches are easily split, and the tree shape is round. Leaves are thick with an oval or fusiform shape and there are weakly developed wings on the petiole. As the fruit reaches maturity, it turns yellow, and the ratio of sugar to acid increases and aroma becomes strong.

In mixed herbal medicine preparation step (S10), the mixed herbal medicine may include 1 to 5% by weight of the antler, 1 to 5% by weight of the *Angelica gigas* root, 1 to 5% by weight of the *Cornus officinalis* fruit, 3 to 7% by weight of the *Rehmannia glutinosa* root, 3 to 7% by weight of the *Lepidium meyenii* root powder, 3 to 7% by weight of the hawthorn fruit, 1 to 5% by weight of the *Astragalus membranaceus* root, 0.1 to 2% by weight of the cod seed, 0.1 to 2% by weight of the aloeo wood, 1 to 5% by weight of the *Paeonia lactiflora* root, 1 to 2% by weight of the *Cnidium officinale* root stem and 1 to 5% by weight of the *Citrus reticulata* shell. Purified water may be included as the balance.

More preferably, in mixed herbal medicine preparation step (S10), the mixed herbal medicine may include 3.7% by weight of the antler, 3.7% by weight of the *Angelica gigas* root, 3.7% by weight of the *Cornus officinalis* fruit, 4.8% by weight of the *Rehmannia glutinosa* root, 4.8% by weight of the *Lepidium meyenii* root powder, 4.8% by weight of the hawthorn fruit, 2.5% by weight of the *Astragalus membranaceus* root, 1% by weight of the cod seed, 0.5% by weight of the aloeo wood, 3.7% by weight of the *Paeonia lactiflora* root, 1.7% by weight of the *Cnidium officinale* root stem and 2.5% by weight of the *Citrus reticulata* shell. Purified water may be included as the balance.

It will be desired to clean and mix the herbal medicines mixed in mixed herbal preparation step (S10).

Next, mixed herbal medicine extract preparation step (S20) of extracting the mixed herbal medicine of step (S10) in a vacuum state to prepare a mixed herbal medicine extract is performed.

In step (S20), 2500 to 3000 cc of extraction solvent is added to the mixed herbal medicine including bellflower, jujube, quince, peppermint top, dried *Houttuynia cordata* top, loquat leaf, *Glehnia* root, *Rehmannia glutinosa* root, *Cnidium officinale* root, *Angelica gigas* root, cinnamon branch, and ginger root and the mixed herbal medicine is extracted in a vacuum state for 220 to 260 minutes at a temperature of 115 to 125° C.

As the extraction solvent, one or more of water, alcohol having 1 to 4 carbon atoms, methanol, ethanol, butanol, and propanol may be selected and mixed to use. Preferably, water and ethanol are mixed in a weight ratio of 7:3.

If the amount of extraction solvent in step (S20) is less than 2500 cc, the amount of the extract is too small, and if the amount of extraction solvent exceeds 3000 cc, the concentration of the extract is too low, so that the final resultant effect is lowered.

It is desired to maintain the temperature at 115 to 125° C. in step (S20). If the temperature is less than 115° C., the temperature is too low to properly extract the mixed herbal medicine, and if the temperature exceeds 125° C., the temperature is too high to accurately get the effect of the final resultant because the properties of the mixed herbal medicine may be changed.

In addition, the extraction time is desirably set to 220 to 260 minutes in step (S20). If the extraction time is less than 220 minutes, the extraction does not sufficiently performed, so the concentration of the extract is low, lowering the effect of the final resultant, and if the extraction time exceeds 260 minutes, it is economically inefficient because most of the extraction has already been made.

The above extraction conditions are optimum extraction conditions that allow the mixed herbal medicine to represent the optimum effect when it is obtained by mixing antler, an *Angelica gigas* root, a *Cornus officinalis* fruit, a *Rehmannia glutinosa* root, *Lepidium meyenii* root powder, a hawthorn fruit, an *Astragalus membranaceus* root, a cod seed, aloeo wood, a *Paeonia lactiflora* root, a *Cnidium officinale* root stem and a *Citrus reticulata* shell.

Next, a mixed herbal medicine concentrate preparation step (S30) of preparing a mixed herbal medicine concentrate by concentrating the mixed herbal medicine extract of step (S20) is performed.

It is desired that step (S30) is performed in a low-temperature concentration method.

In step (S30), 2500 cc to 3000 cc of the mixed herbal medicine extract is made into 600 cc to 900 cc of mixed herbal medicine concentrate through the by low-temperature concentration method.

In step (S30), stirring may be performed in the process of concentrating the mixed herbal medicine extract.

The low-temperature concentration method of step (S30) may be performed at a temperature of 55 to 75° C. in a vacuum state through a vacuum low-temperature concentrator to concentrate components affected by heat or components oxidized by air.

Then, a liquid tea, soft extract and syrup preparation step (S40) is performed to prepare liquid tea, soft extract, and syrup by mixing the mixed herbal medicine concentrate of step (S30) with oligosaccharide and DL-menthol.

In this case, the liquid tea, soft extract, and syrup may include 1 to 5% by weight of the antler, 1 to 5% by weight of the *Angelica gigas* root, 1 to 5% by weight of the *Cornus officinalis* fruit, 3 to 7% by weight of the *Rehmannia glutinosa* root, 3 to 7% by weight of the *Lepidium meyenii* root powder, 3 to 7% by weight of the hawthorn fruit, 1 to 5% by weight of the *Astragalus membranaceus* root, 0.1 to 2% by weight of the cod seed, 0.1 to 2% by weight of the aloeo wood, 1 to 5% by weight of the *Paeonia lactiflora* root, 1 to 2% by weight of the *Cnidium officinale* root stem and 1 to 5% by weight of the *Citrus reticulata* shell. In addition, oligosaccharides may be included as the balance.

The oligosaccharide is a sugar polymer containing a small number (2 to 10) of monosaccharides. In general, the oligosaccharides exist in the form of glycan and are linked to the amino acid side branches of fats or proteins, and are generally found in two forms: N-linked or O-linked oligosaccharides. The N-linked oligosaccharides are found as being attached to asparagine through the beta bond of amine nitrogen on the side branch. The O-linked oligosaccharides are generally attached to the side branch alcohol group of the threonine or serine group. Oligosaccharides perform many functions such as cell recognition and cell binding.

Meanwhile, most preferably, the oligosaccharide in liquid tea, soft extract, and syrup preparation step (S40) is isomalto oligosaccharide. The isomalto oligosaccharide is produced by decomposing starch such as corn and rice. Among the ingredients excluding water, 20 to 40% is oligosaccharide, but the rest is composed of glucose, malto oligosaccharide, dextrin powder, etc., as a starch decomposition product. The isomalto oligosaccharide is a substance that can help in the proliferation of beneficial bacteria in the intestine and suppression of harmful bacteria, and has an effect that can help smooth defecation activity.

Meanwhile, the dl-menthol (DL-Mentol) is a flavoring agent belonging to the aliphatic higher alcohols, and is used in beverages, ice cream, gum, and the like. The dl-menthol is a colorless columnar or needle-shaped crystal or white crystalline powder, which has a peculiar and refreshing aroma, is slightly bitter at first and then has a refreshing taste. The chemical formula of dl-menthol is $C10H20O$. It is rarely dissolved in water and soluble in organic solvents and hydrochloric acid. The dl-menthol has sublimable and non-rotatory polarization properties. The dl-menthol has a freezing point of 27 to 28° C., a melting point of 32 to 38° C., a boiling point of 103 to 105° C., and a refractive index (n(20, D)) of 1.4615. The acceptable daily intake (ADI) of dl-menthol is 0.0 to 0.2 mg/kg. When administered orally to rats, LD50 is 3.18 g/kg. The dl-menthol is used in beverages, ice cream, and gum, and it needs to be used only for flavoring purposes. Since the dl-menthol has a property of volatilization, it is stored in a sealed container and stored in a cool and dark place.

In syrup preparation step (S40), the mixed herbal medicine concentrate is mixed with oligosaccharide, dl-menthol, etc. to prepare the liquid tea, soft extract, and syrup, and then the liquid tea, soft extract, and syrup are packaged with sticks, etc. such that they can be provided to the user. Users may use drink it as tea by dissolving it in water.

In addition, one aspect of the present disclosure provides a functional food composition having a cranial nerve protective effect and a blood flow improvement effect, which is prepared by the above preparation method.

The functional food composition having a cranial nerve protective effect and a blood flow improvement effect according to one aspect of the present disclosure may include 1 to 5% by weight of the antler, 1 to 5% by weight of the *Angelica gigas* root, 1 to 5% by weight of the *Cornus officinalis* fruit, 3 to 7% by weight of the *Rehmannia glutinosa* root, 3 to 7% by weight of the *Lepidium meyenii* root powder, 3 to 7% by weight of the hawthorn fruit, 1 to 5% by weight of the *Astragalus membranaceus* root, 0.1 to 2% by weight of the cod seed, 0.1 to 2% by weight of the aloeo wood, 1 to 5% by weight of the *Paeonia lactiflora* root, 1 to 2% by weight of the *Cnidium officinale* root stem and 1 to 5% by weight of the *Citrus reticulata* shell. In addition, oligosaccharides may be included as the balance.

Most preferably, the functional food composition having a cranial nerve protective effect and a blood flow improvement effect according to one aspect of the present disclosure may include 3.7% by weight of the antler, 3.7% by weight of the *Angelica gigas* root, 3.7% by weight of the *Cornus officinalis* fruit, 4.8% by weight of the *Rehmannia glutinosa* root, 4.8% by weight of the *Lepidium meyenii* root powder, 4.8% by weight of the hawthorn fruit, 2.5% by weight of the *Astragalus membranaceus* root, 1% by weight of the cod seed, 0.5% by weight of the aloeo wood, 3.7% by weight of the *Paeonia lactiflora* root, 1.7% by weight of the *Cnidium officinale* root stem, 2.5% by weight of the *Citrus reticulata* shell, 0.1% by weight of the DL-menthol and 62.5% by weight of the oligosaccharide.

Hereinafter, the effects of the functional food composition having a cranial nerve protective effect and a blood flow improvement effect, which is prepared according to one aspect of the present disclosure, will be described in detail with reference to the following Preparation Examples, Comparative Examples and Experimental Examples.

Preparation Example 1. Preparation of Extraction Solvent

The extraction solvent was prepared by mixing purified water and ethanol in a ratio of 7:3 by weight.

Example 1. Preparation of Functional Food Composition Having Cranial Nerve Protective Effect and Blood Flow Improvement Effect According to One Aspect of the Present Disclosure A functional food composition having a cranial nerve protective effect and a blood flow improvement effect of Example 1 was prepared according to the following preparation method.

(S10): A mixed herbal medicine was prepared by mixing 3.7% by weight of the antler, 3.7% by weight of the *Angelica gigas* root, 3.7% by weight of the *Cornus officinalis* fruit, 4.8% by weight of the *Rehmannia glutinosa* root, 4.8% by weight of the *Lepidium meyenii* root powder, 4.8% by weight of the hawthorn fruit, 2.5% by weight of the *Astragalus membranaceus* root, 1% by weight of the cod seed, 0.5% by weight of the aloeo wood, 3.7% by weight of the *Paeonia lactiflora* root, 1.7% by weight of the *Cnidium officinale* root stem, 2.5% by weight of the *Citrus reticulata* shell and the balance of purified water.

(S20): A mixed herbal medicine extract was obtained by adding 2700 cc of the extraction solvent of Preparation Example 1 to the mixed herbal medicine of step (S10) and extracting the mixture in a vacuum state at a temperature of 120° C. for 240 minutes.

(S30): A mixed herbal concentrate was prepared by concentrating 2700 cc of the mixed herbal medicine extract of step (S20) in a low-temperature vacuum concentrator at 70° C.

(S40): Syrup was prepared by mixing the mixed herbal medicine concentrate of step (S30) with isomalto oligosaccharide and DL-menthol.

Comparative Example 1. Preparation of Composition Containing Only Antler as Active Ingredient In order to compare with Example 1, a composition containing only the antler as an active ingredient was prepared. The procedure the same as Example 1 was carried out, except that the amount of the antler was 37.4% by weight different from the mixed herbal medicine in step (S10), the purified water was filled as the balance and the extraction was performed. For fair comparison, the rest of the preparation process was performed in the same manner as in Example 1.

Comparative Example 2. Preparation of Composition Containing Only *Angelica gigas* Root as Active Ingredient In order to compare with Example 1, a composition containing only the *Angelica gigas* root as an active ingredient was prepared. The procedure the same as Example 1 was carried out, except that the amount of the *Angelica gigas* root was 37.4% by weight different from the mixed herbal medicine in step (S10), the purified water was filled as the balance and the extraction was performed. For fair comparison, the rest of the preparation process was performed in the same manner as in Example 1.

Comparative Example 3. Preparation of Composition Containing Only *Cornus officinalis* Fruit as Active Ingredient In order to compare with Example 1, a composition containing only the *Cornus officinalis* fruit as an active ingredient was prepared. The procedure the same as Example 1 was carried out, except that the amount of the *Cornus officinalis* fruit was 37.4% by weight different from the mixed herbal medicine in step (S10), the purified water was filled as the balance and the extraction was performed. For fair comparison, the rest of the preparation process was performed in the same manner as in Example 1.

Comparative Example 4. Preparation of Composition Containing Only *Rehmannia glutinosa* Root as Active Ingredient In order to compare with Example 1, a composition containing only the *Rehmannia glutinosa* root as an active ingredient was prepared. The procedure the same as Example 1 was carried out, except that the amount of the *Rehmannia glutinosa* root was 37.4% by weight different from the mixed herbal medicine in step (S10), the purified water was filled as the balance and the extraction was performed. For fair comparison, the rest of the preparation process was performed in the same manner as in Example 1.

Comparative Example 5. Preparation of Composition Containing Only *Lepidium meyenii* Root Powder as an Active Ingredient In order to compare with Example 1, a composition containing only the *Lepidium meyenii* root powder as an active ingredient was prepared. The procedure the same as Example 1 was carried out, except that the amount of the *Lepidium meyenii* root powder was 37.4% by weight different from the mixed herbal medicine in step (S10), the purified water was filled as the balance and the extraction was performed. For fair comparison, the rest of the preparation process was performed in the same manner as in Example 1.

Comparative Example 6. Preparation of Composition Containing Only Hawthorn Fruit as Active Ingredient In order to compare with Example 1, a composition containing only the hawthorn fruit as an active ingredient was prepared. The procedure the same as Example 1 was carried out, except that the amount of the hawthorn fruit was 37.4% by weight different from the mixed herbal medicine in step (S10), the purified water was filled as the balance and the extraction was performed. For fair comparison, the rest of the preparation process was performed in the same manner as in Example 1.

Comparative Example 7. Preparation of Composition Containing Only *Astragalus membranaceus* Root as an Active Ingredient In order to compare with Example 1, a composition containing only the *Astragalus membranaceus* root as an active ingredient was prepared. The procedure the same as Example 1 was carried out, except that the amount of the *Astragalus membranaceus* root was 37.4% by weight different from the mixed herbal medicine in step (S10), the purified water was filled as the balance and the extraction was performed. For fair comparison, the rest of the preparation process was performed in the same manner as in Example 1.

Comparative Example 8. Preparation of Composition Containing Only Cod Seed as Active Ingredient In order to compare with Example 1, a composition containing only the cod seed as an active ingredient was prepared. The procedure the same as Example 1 was carried out, except that the amount of the cod seed was 37.4% by weight different from the mixed herbal medicine in step (S10), the purified water was filled as the balance and the extraction was performed. For fair comparison, the rest of the preparation process was performed in the same manner as in Example 1.

Comparative Example 9. Preparation of Composition Containing Only Aloe Wood as Active Ingredient In order to compare with Example 1, a composition containing only the aloe wood as an active ingredient was prepared. The procedure the same as Example 1 was carried out, except that the amount of the aloe wood was 37.4% by weight different from the mixed herbal medicine in step (S10), the purified water was filled as the balance and the extraction was performed. For fair comparison, the rest of the preparation process was performed in the same manner as in Example 1.

Comparative Example 10. Preparation of Composition Containing Only *Paeonia lactiflora* Root as Active Ingredient In order to compare with Example 1, a composition containing only the *Paeonia lactiflora* root as an active ingredient was prepared. The procedure the same as Example 1 was carried out, except that the amount of the *Paeonia lactiflora* root was 37.4% by weight different from the mixed herbal medicine in step (S10), the purified water was filled as the balance and the extraction was performed. For fair comparison, the rest of the preparation process was performed in the same manner as in Example 1.

Comparative Example 11. Preparation of Composition Containing Only *Cnidium officinale* Root Stem as Active Ingredient In order to compare with Example 1, a composition containing only the *Cnidium officinale* root stem as an active ingredient was prepared. The procedure the same as Example 1 was carried out, except that the amount of the *Cnidium officinale* root stem was 37.4% by weight different from the mixed herbal medicine in step (S10), the purified water was filled as the balance and the extraction was performed. For fair comparison, the rest of the preparation process was performed in the same manner as in Example 1.

Comparative Example 12. Preparation of Composition Containing Only *Citrus reticulata* Shell as Active Ingredient In order to compare with Example 1, a composition containing only the *citrus reticulata* shell as an active ingredient was prepared. The procedure the same as Example 1 was carried out, except that the amount of the *Citrus reticulata* shell was 37.4% by weight different from the mixed herbal medicine in step (S10), the purified water was filled as the balance and the extraction was performed. For fair comparison, the rest of the preparation process was performed in the same manner as in Example 1.

Experimental Example 1. Blood Flow Improvement Effect

In order to find out the effect of improving the blood flow of the composition according to one aspect of the present disclosure, experiments were performed on the compositions prepared in Example 1 and Comparative Examples 1 to 12.

Meanwhile, with respect to 100 men having a total carotid artery average blood flow rate of 19 to 22 cm/s without chronic disease and agreed to participate in the experiment, 10 ml of the composition prepared in Example 1 and Comparative Examples 1 to 12 was oral-administered twice a day (10 Am and 5 Pm) over 5 days. The blood flow was measured before administration of the composition, and the blood flow was measured at an interval of 5 days while administering the composition for 15 days, and the results of the average values are shown in Table 1 below.

TABLE 1

| | Blood flow (cm/s) | | | |
|---|---|---|---|---|
| | Before administration | 5 days later | 10 days later | 15 days later |
| Example 1 | 18.2 | 20.5 | 22.4 | 24.2 |
| Comparative Example 1 | 18.3 | 18.6 | 18. | 19.4 |
| Comparative Example 2 | 18.2 | 18.5 | 18.9 | 19.2 |
| Comparative Example 3 | 18.1 | 18.5 | 18.8 | 19.7 |
| Comparative Example 4 | 18.2 | 18.7 | 18.8 | 19.2 |
| Comparative Example 5 | 18.2 | 18.4 | 18.7 | 19.4 |
| Comparative Example 6 | 18.3 | 18.5 | 18.8 | 19.8 |
| Comparative Example 7 | 18.2 | 18.6 | 18.9 | 19.2 |
| Comparative Example 8 | 18.2 | 18.7 | 18.7 | 19.5 |
| Comparative Example 9 | 18.3 | 18.5 | 18.8 | 19.6 |
| Comparative Example 10 | 18.2 | 18.4 | 18.9 | 19.5 |
| Comparative Example 11 | 18.1 | 18.4 | 18.7 | 19.1 |
| Comparative Example 12 | 18.2 | 18.4 | 18.9 | 19.3 |

As shown in Table 1, Comparative Examples 1 to 12 had insignificant effect of improving the blood flow, but it was confirmed that Example 1 clearly showed the effect of improving the blood flow. This is because the effect obtained by mixing the antler, *Angelica gigas* root, *Cornus officinalis* fruit, *Rehmannia glutinosa* root, *Lepidium meyenii* root powder, hawthorn fruit, *Astragalus membranaceus* root, cod seed, aloeo wood, *Paeonia lactiflora* root, *Cnidium officinale* root stem and *Citrus reticulata* shell is higher than the effect obtained from each of the above components and it is estimated that unexpected effects occurred through the reaction between the components in the process of mixing and extracting the components.

Experimental Example 2. Measurement of Cranial Neuroprotective Action by Oral Administration of Sample in Transient Local Cerebral Ischemia Animal Model The measurement of cranial neuroprotective action by oral administration of a sample in the transient local cerebral ischemia animal model was carried out as follows according to a known method.

Experimental animals were 7-week-old sprague-dawly male rats having a weight of 260 to 270 g and the experimental animals were adapted in the breeding room for 7 days before use under the environment in which the contrast cycle was controlled automatically by 12 hours. The temperature of the breeding room was maintained at 23±2° C., the humidity was 55±10%, and food and water were freely ingested.

In order to measure the neuroprotective action according to the oral administration of the sample, an animal model of cerebral ischemia was created. The middle cerebral artery occlusion (MCAO) surgery was performed to create the animal model of cerebral ischemia. Cerebral ischemia was maintained for 22 hours by closing the middle cerebral artery for 120 minutes and performing reperfusion. The body temperature was maintained at 37±0.5° C. using a heating pad and a heating lamp to prevent the body temperature from dropping in all surgical procedures. The sample was oral-administered by dissolving or suspending the compositions prepared in Example 1 and Comparative Examples 1 to 12 in physiological saline 2 hours after induction of cerebral ischemia and 2 hours after reperfusion, and 10 mg/kg of MCI-186, which is known as a treatment agent for acute stroke, was oral-administered as a positive control group. In addition, as a control group, physiological saline was oral-administered in the same amount as the samples.

In order to measure the neuroprotective action of the sample according to the oral administration, the brain was excised 24 hours after the middle cerebral artery occlusion and stained with 2,3,5-triphenyltetrazolium chloride. The stained brain sections were immersed in 10% formalin neutral buffer solution and fixed, and then stored in a computer. The area of cerebral infarction (infarct area, $mm^2$) was measured using a computerized image analyzer, and the infarct volume ($mm^3$) was calculated by multiplying the total sum of the infarct area of each section by the thickness of the section. The measured values were expressed as mean±SEM (*$p<0.05$, **$p<0.01$).

TABLE 2

|  | Cerebral infarct volume (mm³) | Cranial nerve protection effect (%) |
| --- | --- | --- |
| Physiological saline administration group | 352.3 ± 15.2 | — |
| MCI-186 administration group | 184.2 ± 17.3** | 47.71 |
| Example 1 Administration group | 164.2 ± 16.1** | 53.39 |
| Comparative Example 1 | 240.3 | 32.79 |
| Comparative Example 2 | 253.2 | 28.12 |
| Comparative Example 3 | 251.6 | 28.58 |
| Comparative Example 4 | 238.3 | 32.35 |
| Comparative Example 5 | 256.8 | 27.10 |
| Comparative Example 6 | 272.3 | 22.70 |
| Comparative Example 7 | 287.2 | 18.47 |
| Comparative Example 8 | 257.7 | 26.85 |
| Comparative Example 9 | 271.3 | 16.60 |
| Comparative Example 10 | 262.5 | 25.48 |
| Comparative Example 11 | 307.3 | 12.77 |
| Comparative Example 12 | 256.3 | 27.24 |

As shown in Table 2, Comparative Examples 1 to 12 had insignificant effects of protecting the cranial nerves, but Example 1 clearly showed an effect of protecting the cranial nerves and had a higher cranial nerve protective effect than MCI-186 which is the positive control group. This is because the effect obtained by mixing the antler, *Angelica gigas* root, *Cornus officinalis* fruit, *Rehmannia glutinosa* root, *Lepidium meyenii* root powder, hawthorn fruit, *Astragalus membranaceus* root, cod seed, aloeo wood, *Paeonia lactiflora* root, *Cnidium officinale* root stem and *Citrus reticulata* shell is higher than the effect obtained from each of the above components and it is estimated that unexpected effects occurred through the reaction between the components in the process of mixing and extracting the components.

Although the present disclosure has been described with reference to the accompanying drawings, this is only one of various embodiments including the subject matter of the present disclosure, and is intended to be easily implemented by those of ordinary skill in the art. It is clear that the present disclosure is not limited to the above-described embodiments. Accordingly, the scope of protection of the present disclosure has to be interpreted by the following claims, and all technical ideas within the scope equivalent to the present disclosure through the changes, substitutions, modifications, etc. may fall within the right of the present disclosure. In addition, it is clarified that some of the configurations in the drawings may be exaggerated or reduced than in actuality for clearly explaining the configuration.

What is claimed is:

1. A method of preparing a functional food composition having a cranial nerve protective effect and a blood flow improvement effect, the method comprising:
   a mixed herbal medicine preparation step (S10) of preparing a mixed herbal medicine by mixing about 3.7% by weight of antler, about 3.7% by weight of an *Angelica gigas* root, about 3.7% by weight of a *Cornus officinalis* fruit, about 4.8% by weight of a *Rehmannia glutinosa* root, about 4.8% by weight of *Lepidium meyenii* root powder, about 4.8% by weight of a hawthorn fruit, about 2.5% by weight of an *Astragalus membranaceus* root, about 1.0% by weight of a cod seed, about 0.5% by weight of aloeo wood, about 3.7% by weight of a *Paeonia lactiflora* root, about 1.7% by weight of a *Cnidium officinale* root stem, about 2.5% by weight of a *Citrus reticulata* shell, and a balance of purified water;
   a mixed herbal medicine extract preparation step (S20) of preparing a mixed herbal medicine extract by extracting the mixed herbal medicine of step (S10) in a vacuum state at a temperature of 120° C. for 240 minutes after adding 2700 cc of an extraction solvent of purified water and ethanol in a ratio of 7:3 by weight to the mixed herbal medicine of step (S10);
   a mixed herbal medicine concentrate preparation step (S30) of preparing a mixed herbal medicine concentrate by concentrating 2700 cc of the mixed herbal medicine extract of step (S20) in a low-temperature vacuum concentrator at 70° C.; and
   a liquid tea, soft extract, and syrup preparation step (S40) of preparing liquid tea, soft extract, and syrup preparing by mixing the mixed herbal medicine concentrate of step (S30) with isomalto oligosaccharides and DL-menthol.

2. A functional food composition having a cranial nerve protective effect and a blood flow improvement effect, which is prepared according preparing a mixed herbal medicine by mixing about 3.7% by weight of antler, about 3.7% by weight of an *Angelica gigas* root, about 3.7% by weight of a *Cornus officinalis* fruit, about 4.8% by weight of a *Rehmannia glutinosa* root, about 4.8% by weight of *Lepidium meyenii* root powder, about 4.8% by weight of a hawthorn fruit, about 2.5% by weight of an *Astragalus membranaceus* root, about 1.0% by weight of a cod seed, about 0.5% by weight of aloeo wood, about 3.7% by weight of a *Paeonia lactiflora* root, about 1.7% by weight of a *Cnidium officinale* root stem, about 2.5% by weight of a *Citrus reticulata* shell, and a balance of purified water; preparing a mixed herbal medicine extract by extracting the mixed herbal medicine in a vacuum state at a temperature of 120° C. for 240 minutes after adding 2700 cc of an extraction solvent of purified water and ethanol in a ratio of 7:3 by weight to the mixed herbal medicine of step (S10); preparing a mixed herbal medicine concentrate by concentrating 2700 cc of the mixed herbal medicine extract of step (S20) in a low-temperature vacuum concentrator at 70° C.; and preparing the functional food composition by mixing the mixed herbal medicine concentrate with isomalto oligosaccharides and DL-menthol.

* * * * *